United States Patent
Tomany et al.

[11] Patent Number: 5,304,798
[45] Date of Patent: Apr. 19, 1994

[54] HOUSING FOR CONVERTING AN ELECTROSPRAY TO AN ION STREAM

[75] Inventors: Michael J. Tomany, Groseenordale, Conn.; Joseph A. Jarrell, Newton Highlands, Mass.

[73] Assignee: Millipore Corporation, Bedford, Mass.

[21] Appl. No.: 866,618

[22] Filed: Apr. 10, 1992

[51] Int. Cl.⁵ ............................................. H01J 49/04
[52] U.S. Cl. ................... 250/288; 250/281; 250/282
[58] Field of Search ................ 250/281, 282, 288 R, 250/288 A

[56] References Cited
U.S. PATENT DOCUMENTS

| | | | |
|---|---|---|---|
| 4,842,701 | 6/1989 | Smith et al. | 250/288 |
| 4,977,320 | 12/1990 | Chowdhury et al. | 250/288 |
| 4,999,493 | 3/1991 | Allen et al. | 250/288 |
| 5,170,052 | 12/1992 | Kato et al. | 250/288 |

*Primary Examiner*—Jack I. Berman
*Assistant Examiner*—James Beyer
*Attorney, Agent, or Firm*—Paul J. Cook; Andrew T. Karnakis

[57] ABSTRACT

A housing is provided for converting an electrospray into a desolvated ion stream for analysis. The housing is positioned between an electrospray device and an ion stream analytical device. The housing is heated and includes a passageway within which a moving electrospray is converted to the ion stream.

7 Claims, 2 Drawing Sheets

HOUSING FOR CONVERTING AN ELECTROSPRAY TO AN ION STREAM

BACKGROUND OF THE INVENTION

This invention relates to a method and apparatus for producing an ion stream from an electrospray formed from a sample solution and for analyzing the ion stream. More particularly this invention relates to an apparatus for receiving an electrospray and converting it to an ion stream for analysis.

A liquid flowing through a capillary jet or orifice may be converted to a spray of small charged droplets (of the order of 1 $\mu$m in diameter) by applying a strong electric field to the liquid as it emerges from the tip of the capillary. For a sufficiently high applied field, the electrostatic stress imposed by the field and the surface-induced electrical charge is sufficient to overcome the surface tension forces on the liquid. Breaking apart into a large number of small charged droplets is a way for the liquid to disperse the charge and reach a lower total energy state. This process of forming a spray is commonly known as electrospray.

At the present time apparatus are available for forming an electrospray of a sample solution such as a liquid stream effluent from a liquid chromatography separation step and subsequently analyzing the electrospray with a mass analyzer such as a quadrupole mass spectrometer, an ion trap, a time-of-flight mass spectrometer or a magnetic sector mass spectrometer or the like. Interposed between the apparatus for forming the electrospray and the analytical apparatus is means for desolvating the droplets forming the electrospray so as to form a stream of intact ions which are to be analyzed. In a liquid chromatograph, a stream of solvent, containing a mixture of chemical species in solution, is passed at elevated pressure through a chromatographic column. The column is so designed that it separates the mixture, by differential retention on the column, into its component species. The different species then emerge from the column as distinct bands in the solvent stream, separated in time. Coupling the output of a liquid chromatograph to a mass spectrometer via an electrospray interface gives the analyst a powerful tool since it can provide molecular weight and structural information about the separated species as they emerge from the liquid chromatograph.

It has been proposed in U.S. Pat. No. 4,977,320 to interpose a heated capillary tube between the electrospray apparatus and the analytical apparatus to desolvate the electrospray droplets thereby to form the intact ion stream. The apparatus is undesirable since it is difficult to uniformly heat the thin-walled tube. This may result in local "hot spots" which can cause sample degradation. In addition, the capillary can become clogged due to sample deposition therein and it is difficult to clean for subsequent use. Furthermore, mechanical construction and alignment are difficult.

Allen and Vestal disclose in U.S. Pat. No. 4,999,493 (and in "Design and Performance of a Novel Electrospray Interface", Journal of the American Society of Mass Spectrometry 1992, 3, 18-26) the use of an electrospray interface that consists of three chambers interposed between the electrospray capillary and the analytical apparatus. A first spray chamber, a second skimmer chamber and finally a third heated skimmer chamber. It is diclosed that droplet desolvation and consequent ion generation occur in this heated chamber. In practice this apparatus is undesirable because to be effective the heated chamber must be typically at 200-250 C. This high heat level requires the spray chamber to be cooled by circulating water, which adds significantly to the complexity and operating cost of this interface.

Additionally, existing electrospray interfaces typically require the precise positioning of the electrospray capillary with respect to the remaining components of the interface in order to optimize sensitivity.

Accordingly, it would be desirable to provide a method and apparatus for efficiently converting an electrospray into an intact ion stream for subsequent analysis in a mass spectrometer or the like. In addition, it would be desirable to provide such an apparatus wherein the electrospray is substantially desolvated with uniform heating. Furthermore, it would be desirable to provide such an apparatus which can be cleaned, reassembled and realigned easily for subsequent reuse. Further desirable features of such an apparatus include not requiring a cooling means, not requiring precise positioning of the electrospray capillary with respect to the remaining interface components, not requiring an external supply of gas, and not requiring excessively large rotary vacuum pumps.

SUMMARY OF THE INVENTION

The present invention provides a housing which receives an electrospray from an electrospray apparatus, substantially desolvates the electrospray to form an intact ion stream (consisting of comprising ions, vapor and gas) and directs the ion stream to an analytical apparatus. The housing is formed integrally with walls and a skimmer to form a chamber for receiving the ion stream from the housing and for directing it through the skimmer, through another pressure reduction stage, and into the analytical apparatus. The housing is formed of an electrically and thermally conductive material and includes a contoured passageway through its thickness having an entrance for the electrospray and an exit into the chamber for the ion stream. The housing is heated so that the electrospray within the passageway is substantially desolvated to produce an ion stream and which exits into the chamber adjacent a skimmer. A partial vacuum is maintained in the chamber. The ion stream passes from the chamber, through the skimmer, through the additional pressure reduction stage, and into the analyzer. The analyzer is capable of analyzing the mass-to-charge spectrum of the sample solute.

DESCRIPTION OF SPECIFIC EMBODIMENTS

Figure 1:
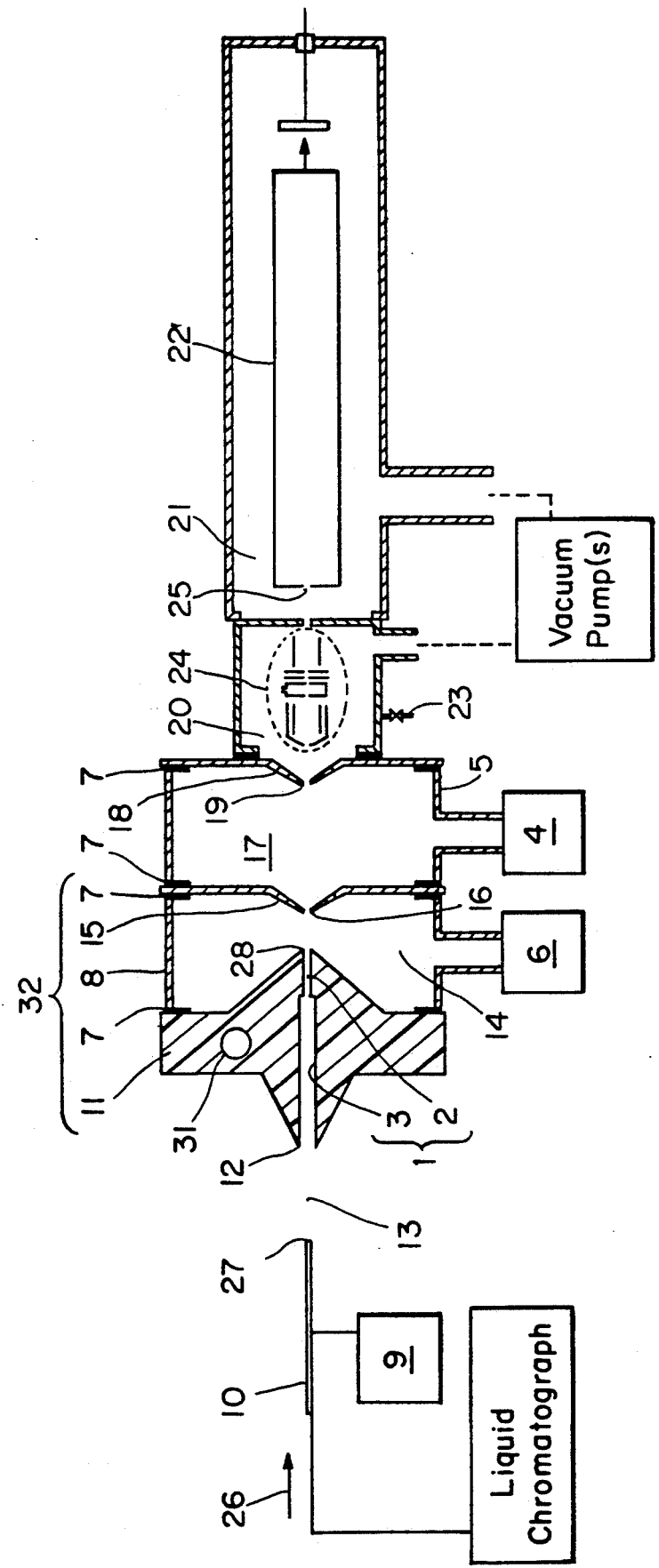
FIG. 1 is a schematic view of a preferred apparatus of this invention.

The present invention provides a heated housing which includes a contoured passageway through its thickness to effect passage of an electrospray therethrough. The housing is formed of an electrically and thermally conductive material which is heated to a temperature between about 65° C. and 220° C., preferably between about 100° C. and 130° C. The housing can ideally be formed of a metal of high thermal conductivity such as aluminum. The housing can be heated by a conventional means such as by electrical resistance heaters imbedded in the housing and surrounding the passageway or by internal conduits for heat exchange fluid. In any event, uniform heating of the passageway can be easily effected due to its mass and material of construction. The passageway through the housing is contoured in such a way as to reduce the need for precise positioning of the electrospray capillary with respect to the housing and to optimize thermal transfer from the housing to the ion steam. Other specific benefits conferred by this design compared to previous designs are the elimination of the need for any external supply of gas, ease of disassembly, cleaning and alignment, and the ability to provide useful data with relatively modest rotary pumps.

Typically, the overall length of the passageway within the housing is between about 1 and 4 cm. Gas from the atmosphere is entrained into the entrance end of the passageway by effecting a partial vacuum within a chamber formed by walls which include the housing of this invention and a skimmer.

Conventionally, as practiced by others, the electrospray capillary which houses the liquid sample is formed from an electrically conductive item material, such as a stainless steel hypodermic needle. In a preferred form of the invention, the portion of the electrospray which houses the liquid sample is formed from an electrically insulating material such as glass, quartz, synthetic polymeric composition or the like. The use of an electrically insulating material provides substantial advantage over the use of an electrically conductive material to house the liquid in the electrospray device such as stainless steel. In one mode of operation, the electrospray can be effected at low voltages with a capillary or jet having a small outer diameter in the order of 10 $\mu$m to 20 $\mu$m. Electrospray can be produced at an applied potential difference as low as about 775 volts between the electrospray device exit and the nearest reference electrode. In a second mode of operation, it is desirable to maintain as high a voltage differential as possible between the exit end of an electrically insulated electrospray device and the housing. A high voltage of up to about 18 kilovolts (KV) can be used with the nonconducting electrospray. When operating in this manner, high throughputs of electrospray of up to about 20 $\mu$L/min can be achieved while avoiding arcing between the electrospray device and the housing. This flexibility in operation permits the apparatus of this invention to be utilized within a wide range of operating conditions, including the electrospraying of solutions of higher water content (as high as 97% v/v).

Figure 2:
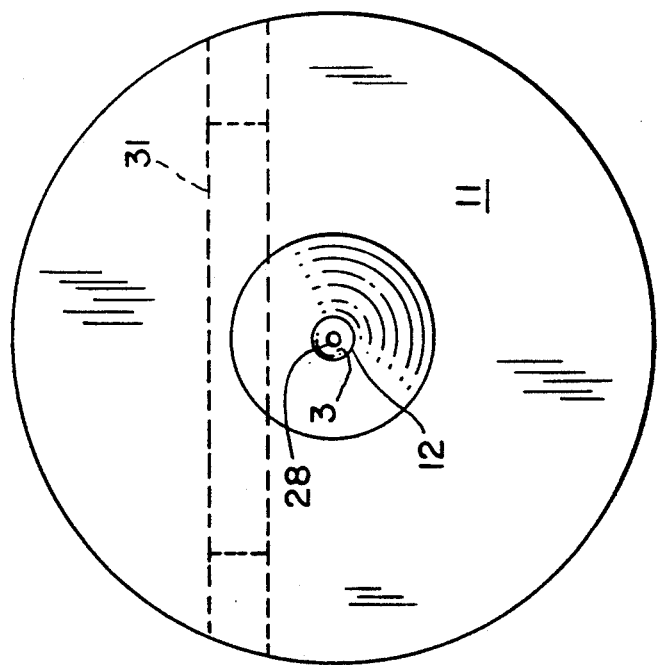
FIG. 2 is a front view of the housing shown in FIG. 1.

Referring to FIGS. 1, and 2, the liquid to be electrosprayed (typically carrying analyte molecules of interest such as from a liquid chromatograph) flows, in the direction shown by the arrow 26, into one end of the passageway electrospray capillary 10 connected to voltage source 9, comprising an electrospray capillary.

As it emerges from the other end of this capillary, the liquid is converted to a spray of electrified droplets and ions, i.e., "electrospray", by virtue of the electrical field imposed at the exit end 27 as a result of an electrical potential difference applied between the exit end 27 at the tip of electrospray capillary passageway 10 and housing 11 which is connected to a voltage supply. This tip 27 from which the liquid is electrosprayed is positioned roughly opposite the heated electrically conductive housing 11 of this invention. Housing 11 comprises a wall for chamber 14 and is electrically insulated by insulating portions 7 from its surrounds and thus may be set at an arbitrary electrical potential with respect to ground. (Typically, this may be accomplished by connecting it to a voltage supply, but other biasing schemes will be evident to those skilled in the art.)

Housing 11 is traversed by a passageway 1 and includes a heater 31 such as an electrical resistance cartridge heater. Passageway 1 has an entrance orifice 12 and an exit orifice 28. Passageway 1 comprises a first region 3 and a second region 2. Since passageway 1 is formed within a housing 11 having significant mass, it can be cleaned easily without deforming unlike the case of a stainless steel capillary or the like capillary. The entrance orifice 12 of passageway 1 is positioned at the apex of housing 11. The housing 11 also serves as a wall between a region of atmospheric pressure 13 and a region of lower pressure 14. Region 14 is maintained at this lower pressure, typically 4–20 Torr by the action of a small rotary pump 6. The housing 11 is typically maintained at a temperature of from 100–130 C. The pressure drop across it causes the ambient atmosphere in region 13 to be drawn toward the orifice 12. This gas flow, in conjunction with the electric field between the electrospray capillary 10 and the housing 11, causes some of the electrosprayed droplets, ions, clusters and vapors to pass through orifice 12 and enter region 3 of passageway 1.

As these droplets pass through the passageway, heat is transferred to them thus promoting desolvation and ion evaporation. The housing 11 has sufficient mass to effect this heat transfer which is typically greater than about 50 g. The volume flow of gas through passageway 1 is determined by atmospheric pressure and by the diameter of region 2 and exit orifice 28. (This situation arrangement is sometimes referred to as choke flow.) The diameter of region 3 may typically be 2–5 times larger than the diameter of region 2. This means that the ion stream velocity in region 3 is typically 4–25 times slower than the ion stream velocity in region 2. (The ion stream velocity in region 3 will be substantially proportional to the square of the ratio of the diameter of region 2 to the diameter of region 3.) This means that the ion stream residence time within the heated housing 11 is many times longer than if the entire passageway 1 were the diameter of region 2. This increased residence time within housing 11 promotes increased thermal transfer from the housing 11 to the ion vapor stream, enhancing desolvation.

In addition, the increased area of orifice 12 reduces the need for precise positioning of the electrospray capillary 10 with respect to housing 11. This results because the gas flow into orifice 12 and the attractive electric fields around orifice 12 are relatively more dispersed (than they would be around were orifice 12 the same diameter of orifice 28) and generate a larger "sweet spot" or acceptance region for the electrospray.

Region 14 is bounded by housing 11, skimmer 15 and wall portion 8. In a preferred embodiment, they are all electrically isolated from each other, by insulating portions 7, such that the shape of wall portion 8, and the electrical potential applied to it, can be used to optimize charged particle transmission. It is, however, also possible for wall portion 8 to be electrically part and/or mechanically part of either housing 11 or skimmer 15. The distance between the exit orifice 28 of passageway 1 and the orifice 16 of skimmer 15 is typically between about 0.1 and 0.5 cm.

The ion stream of air, droplets, ions, gas, clusters, and vapor emerges from orifice 28 into region 14 and impinges on a conductive skimmer 15 that is electrically insulated from its surrounds and thus may be set at an arbitrary electrical potential with respect to ground.

Typically it operates at a potential such that there exists an electrical field between housing 11 and skimmer 15 that tends to focus charged particles towards skimmer 15. Because collisions between charged ion stream components (e.g. ions, charged droplets, charged clusters and solvated ions) and neutral gas molecules occur in this region 14 as the ion stream traverses region 14 on its way to skimmer 15, additional desolvation, ion evaporation and declustering occur. The energy of these collisions can be affected by the potential difference between the housing 11 and skimmer 15.

A portion of the ion stream arriving at skimmer 15 traverses the orifice 16 at its apex and enter region 17 and impinge on a conductive skimmer 18 that is electrically insulated from its surrounds and thus may be set at an arbitrary electrical potential with respect to ground. Region 17 is maintained at a lower pressure, typically 0.1-3 Torr by another rotary pump 4. Again, because collisions between ion stream components (e.g. charged droplets, charged clusters and solvated ions) and neutral gas molecules occur in this region 17 as the ion stream traverses it on its way to skimmer 18, additional desolvation and ion evaporation occurs.

Because of the lower pressure in this region, the energy of these collisions is considerably affected by the potential difference between skimmer 15 and skimmer 18 such that considerable desolvation and ion evaporation may occur.

The energy of collisions in this region can be controlled by the electrical potential difference between these regions. Indeed these collisions can be sufficiently energetic that fragmentation of ionized analyte molecules can occur providing useful structural information.

Region 17 is bounded by skimmer 15, skimmer 18 and wall portion 5. In a preferred embodiment, they are all electrically isolated from each other by insulating portions 7, such that the shape of wall portion 5, and the electrical potential applied to it, can be used to optimize charged particle transmission. It is however, also possible for wall portions 5 to be electrically part and/or mechanically part of either skimmer 15 or skimmer 18.

A portion of the ion stream arriving at skimmer 18 traverses an orifice 19 at the apex of skimmer 18 and enters region 20. Region 20 is typically separated from the region 21 containing the mass spectrometer 22 and each region is separately pumped but this is not mandatory. In other embodiments, regions 20 and 21 may not be separated. In either case, ion optics 24 are contained in region 20 that serve to focus ions, emerging into region 20, via orifice 19, onto the entrance aperture 25 of the mass analyzer 22. Typically, this can be a quadrupole mass spectrometer, an ion trap, a time-of-flight mass spectrometer or a magnetic sector mass spectrometer.

In a preferred embodiment, however, shown in FIG. 1, these ion optics are also designed such that they can also serve to ionize, by conventional electron impact ionization, neutral gas molecules introduced into region 20 through leak valve 23 The benefit provided by this arrangement is that the mass axis of the mass analyzer may be calibrated with well-known, easily purified, low molecular weight compounds, typically perfluorotributylamine.

Figure 3:
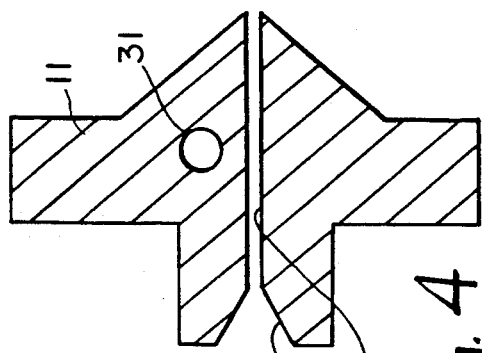
FIG. 3 shows an alternative housing of this invention.
Figure 5:
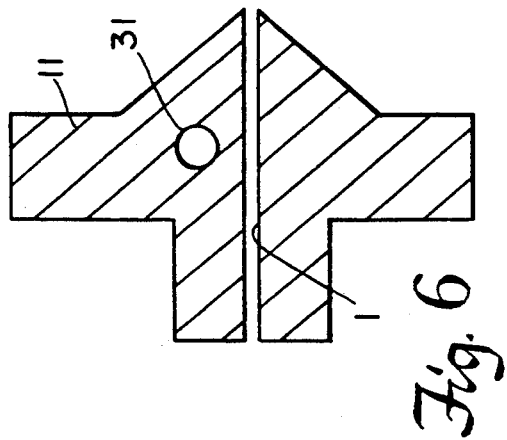
FIG. 5 shows an alternative housing of this invention.
Figure 4:
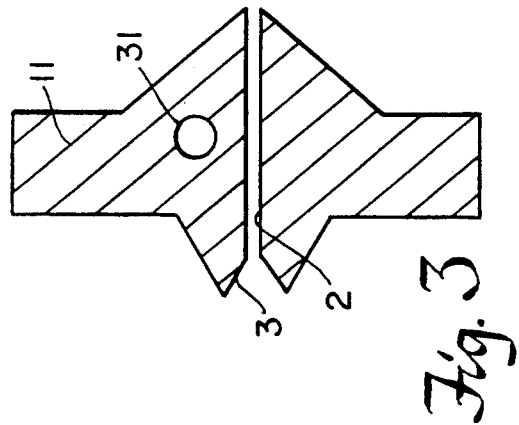
FIG. 4 shows an alternative housing of this invention.
Figure 6:
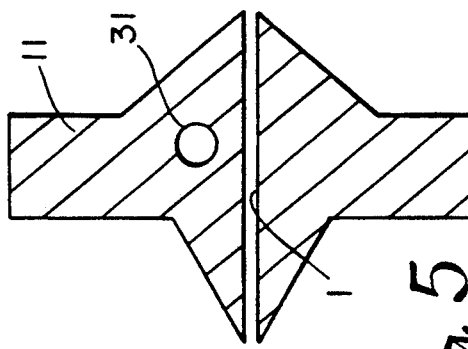
FIG. 6 shows an alternative housing of this invention.

Other variations on housing 11 are possible, as will be evident to someone practiced in the art, and some of these are illustrated in FIGS. 3-6. FIGS. 3 and 4 illustrate different form factors that embody much of the benefits described above. FIGS. 5 and 6 illustrate housings in which, passageway 1 is a straight-through hole. but much of the benefits referred to above (ease of alignment and improved thermal transfer) are lost.

We claim:

1. Apparatus for converting a solution containing a solute sample into ionized molecules for analysis of the sample which comprises
    a first passageway having an orifice for passing said solution therethrough,
    said first passageway having an exit to discharge said solution from said first passageway in the form of an electrospray,
    a voltage source connected to said first passageway orifice,
    an analytical apparatus for measuring charge and mass of ionized molecules,
    an electrically and thermally conductive housing interposed between said first passageway orifice and said analytical apparatus, so that said electrospray passes directly from said exit into a heated second passageway in said housing,
    said housing including said heated second passageway extending through the thickness of said housing to effect conversion of said electrospray to a desolated ion stream,
    said housing having dimensions to form part of a chamber maintained under vacuum and said chamber including a skimmer interposed between said housing and said analytical apparatus.

2. The apparatus of claim 1 wherein said first passageway orifice comprises a capillary tube.

3. The apparatus of claim 2 wherein said capillary tube is formed of an electrically nonconducting material.

4. The apparatus of any one of claims 1, 2, or 3 wherein said housing and said skimmer are electrically insulated from each other.

5. The apparatus of any one of claims 1, 2, or 3 wherein said housing, skimmer and analytical apparatus are electrically insulated from each other.

6. The apparatus of any one of claims 1, 2, or 3 wherein said second passageway has a diameter which varies along the length of said second passageway and wherein a portion of said second passageway having a smaller diameter than a remaining portion of said second passageway is positioned adjacent said skimmer.

7. The apparatus of any one of claims 1, 2, or 3 wherein said second passageway has a constant diameter.

* * * * *